(12) United States Patent
McMichael

(10) Patent No.: US 11,712,403 B2
(45) Date of Patent: Aug. 1, 2023

(54) DISPOSABLE ABSORBENT STOMA PAD FOR GASTROSTOMY

(71) Applicant: O&M Halyard, Inc., Mechanicsville, VA (US)

(72) Inventor: Donald McMichael, Roswell, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 969 days.

(21) Appl. No.: 16/487,152

(22) PCT Filed: Mar. 2, 2017

(86) PCT No.: PCT/US2017/020326
§ 371 (c)(1),
(2) Date: Aug. 20, 2019

(87) PCT Pub. No.: WO2018/160180
PCT Pub. Date: Sep. 7, 2018

(65) Prior Publication Data
US 2020/0022879 A1   Jan. 23, 2020

(51) Int. Cl.
*A61J 15/00*    (2006.01)
(52) U.S. Cl.
CPC .................................. *A61J 15/0065* (2013.01)
(58) Field of Classification Search
CPC .... A61F 13/00042; A61F 5/445; A61F 13/15; A61F 13/00029; A61F 2005/4483; A61F 13/148; A61F 13/00063; A61F 13/00; A61F 13/36; A61F 13/00021; A61F 13/06; A61F 2013/4506; A61F 5/30; A61F 5/443445; A61J 15/00; A61J 15/0015; A61J 15/0049;
(Continued)

(56) References Cited

U.S. PATENT DOCUMENTS

| 4,080,970 A | * | 3/1978 | Miller ................... A61M 27/00 |
|---|---|---|---|
| | | | 604/174 |
| 5,013,307 A | | 5/1991 | Broida |

(Continued)

OTHER PUBLICATIONS

Product Information, Kimberly-Clark® Mic-Key® Low-Profile Gastrostomy Feeding Tube, 2006, 4 pages.
(Continued)

*Primary Examiner* — Amber R Stiles
*Assistant Examiner* — Nelson Louis Alvarado, Jr.
(74) *Attorney, Agent, or Firm* — Dority & Manning, P.A.

(57) ABSTRACT

An absorbent stoma pad for encapsulating an external bolster of a feeding tube is provided. The stoma pad includes an upper layer, base layer, absorbent material, and cavity. The upper layer, which includes an upper surface and a lower surface, contains a centrally located opening with respect to a periphery of the upper layer, wherein the opening is configured to receive a tube portion of the feeding tube. The base layer, which includes an upper surface and a lower surface, contains a centrally located opening with respect to a periphery of the base layer, wherein the opening is also configured to receive the tube portion of the feeding tube. Meanwhile, the absorbent material is disposed adjacent the upper layer's lower surface. Further, the cavity permits airflow between the absorbent layer and the base layer when the external bolster is encapsulated by the stoma pad and positioned within the cavity.

20 Claims, 6 Drawing Sheets

(58) Field of Classification Search
CPC ............... A61J 15/0061; A61J 15/0026; A61J 15/0053; A61J 15/0057; A61J 15/0065; A61J 13/00; A61M 2025/0266; A61M 2025/00273; A61M 25/0017; A61 16/047

See application file for complete search history.

(56) References Cited

U.S. PATENT DOCUMENTS

| | | | |
|---|---|---|---|
| 5,554,106 | A | 9/1996 | Layman-Spillar et al. |
| 6,350,255 | B1 | 2/2002 | von Dyck |
| D500,552 | S | 1/2005 | Peterson et al. |
| 7,985,205 | B2 | 7/2011 | Adams |
| 8,764,714 | B2 | 7/2014 | Fabo et al. |
| 9,084,696 | B2 | 7/2015 | Luce |
| 9,289,322 | B2 | 3/2016 | Lam |
| 9,314,377 | B2 | 4/2016 | Coulthard et al. |
| 2003/0032932 | A1 | 2/2003 | Stout |
| 2003/0225387 | A1 | 12/2003 | Zedlitz |
| 2005/0215948 | A1* | 9/2005 | Adams ............... A61J 15/0015 604/93.01 |
| 2006/0020234 | A1 | 1/2006 | Chou et al. |
| 2007/0239104 | A1 | 10/2007 | Feerrar et al. |
| 2009/0287133 | A1* | 11/2009 | LaGreca, Sr. ...... A61F 13/00063 601/84 |
| 2009/0320852 | A1 | 12/2009 | Cuevas et al. |
| 2010/0256545 | A1* | 10/2010 | Aali ................ A61F 13/0203 604/304 |
| 2011/0270205 | A1* | 11/2011 | Odermatt .......... A61F 13/15211 604/374 |
| 2012/0123379 | A1 | 5/2012 | Forsell |
| 2012/0167893 | A1* | 7/2012 | Schulz ............. A61M 16/0465 128/207.14 |
| 2013/0261587 | A1* | 10/2013 | Clifford ............ A61F 13/00021 604/385.01 |
| 2013/0345654 | A1 | 12/2013 | Bach et al. |
| 2014/0220843 | A1 | 8/2014 | Liu et al. |
| 2015/0250931 | A1 | 9/2015 | Bharti et al. |
| 2016/0120706 | A1 | 5/2016 | Collinson et al. |
| 2016/0175156 | A1* | 6/2016 | Locke ................ A61F 13/0216 604/319 |
| 2021/0161725 | A1* | 6/2021 | Edwards |

OTHER PUBLICATIONS

Naik et al., "Complications of PEG-Prevention and Management", The Internet Journal of Gastroenterology, vol. 8, No. 1, 2008, 10 pages.

International Search Report and Written Opinion for PCT/US2017/020326, dated Dec. 18, 2017, 10 pages.

* cited by examiner

DISPOSABLE ABSORBENT STOMA PAD FOR GASTROSTOMY

RELATED APPLICATION

The present application is the national stage entry of International Patent Application No. PCT/US2017/020326 having a filing date of Mar. 2, 2017, which is incorporated herein by reference in its entirety.

FIELD OF THE INVENTION

The present invention relates to absorbent articles used in conjunction with enteral feeding devices. More particularly, the present invention relates to a stoma pad for pulling fluids away from a stoma site and promoting air flow at the stoma site.

BACKGROUND OF THE INVENTION

Numerous situations exist in which interior parts of the human body needs to be catheterized through an artificial stoma to achieve a desired medical goal. Relatively common situations are for drainage of retained fluids and administering nutritional solutions or medicines directly into the stomach or intestines. For these situations a stoma is formed percutaneously and an indwelling device is placed through the stoma. By way of example, the surgical opening and/or the procedure to create a stoma spanning between the stomach or intestinal wall and the exterior of the skin is commonly referred to as "gastrostomy." A device with a catheter component, e.g., a feeding tube, placed through such a stoma allows injection of feeding solutions through the tube to provide nutrients directly to the stomach or intestines (known as enteral feeding). A variety of different devices intended for enteral feeding have been developed over the years, including some having a "low profile" relative to that portion which sits on a patient's skin, as well as those having the more traditional or non-low profile configuration. These percutaneous transconduit devices (sometimes referred to as "percutaneous transconduit catheters") are frequently referred to as "gastrostomy tubes," "percutaneous gastrostomy tubes," "PEG tubes," or "enteral feeding tubes." These devices, which can also be referred to as feeding tubes, can have an external bolster that rests against the surface of the patient's skin and an internal bolster or balloon that rests against the stomach wall to hold the device in place at the stoma site.

One problem with the use of these feeding tubes is that fluid can leak from the stoma site. The leakage of fluid can be more prevalent in patients with diabetes or patients who are malnourished, as these patients tend to have poor tissue healing and are susceptible to wound breakdown. However, stomal leakage can also occur in the healthiest of patients. In any event, when stomal leakage occurs, moisture can be trapped between the external bolster and the surface of the patient's skin, which can lead to wound infections and poor stoma health. Further, placing, for example, a gauze pad between the external bolster and the skin surface can further degrade stoma health because the gauze can undesirably trap moisture against the skin.

Accordingly, an absorbent stoma pad that pulls fluids away from a stoma site and promotes air flow at the stoma site would be useful. More particularly, an absorbent stoma pad that prevents fluid from sitting against the patient's skin would be beneficial.

SUMMARY OF THE INVENTION

Aspects and advantages of the invention will be set forth in part in the following description, or may be obvious from the description, or may be learned through practice of the invention.

In one particular embodiment, the present invention is directed to an absorbent stoma pad for encapsulating an external bolster of a feeding tube, wherein the feeding tube further includes a tube portion and is positioned above a surface of skin. The absorbent stoma pad includes an upper layer having an upper surface and a lower surface, wherein the upper layer contains an opening that is centrally located with respect to a periphery of the upper layer, wherein the opening is configured to receive the tube portion of the feeding tube; a base layer having an upper surface and a lower surface, wherein the base layer contains an opening that is centrally located with respect to a periphery of the base layer, wherein the opening is configured to receive the tube portion of the feeding tube; an absorbent material disposed adjacent the lower surface of the upper layer; and a cavity separating the absorbent layer and the base layer, wherein the cavity permits airflow between the absorbent layer and the base layer when the external bolster is encapsulated by the absorbent stoma pad and positioned within the cavity.

In one embodiment, the lower surface of the base layer can contact the surface of skin when the external bolster is encapsulated by the upper layer and the base layer of the absorbent stoma pad.

In another embodiment, the upper layer can include a nonwoven material. For example, the upper layer can include a spunbond-meltblown-spunbond laminate.

In yet another embodiment, the base layer can be a wicking layer. Further, the wicking layer can include rayon, polyester, a polyolefin, an aliphatic ester, or a combination thereof.

In still another embodiment, skin health additives can be incorporated into the base layer.

In one more embodiment, the absorbent material can be a superabsorbent material. For instance, the superabsorbent material can include poly(acrylic acid), poly(methacrylic acid), poly(acrylamide), poly(vinyl ether), a maleic anhydride copolymer with a vinyl ether and an α-olefin, poly (vinyl pyrrolidone), poly(vinylmorpholinone), poly(vinyl alcohol), hydrolyzed acrylonitrile-grafted starch, acrylic acid-grafted starch, methyl cellulose, chitosan, carboxymethyl cellulose, hydroxypropyl cellulose, alginate, xanthan gum, locust bean gum, or a combination thereof.

In an additional embodiment, skin health additives can be incorporated into the absorbent material.

In one particular embodiment, the upper layer can include a slit extending from the opening to the periphery of the upper layer. Further, a fastening means can be disposed on the lower surface of the upper layer along the slit.

In one embodiment, a fastening means can be disposed on the lower surface of the upper layer about the periphery of the upper layer.

In another embodiment, the fastening means can have a hook or loop configuration.

In yet another embodiment, the base layer can include a slit extending from the opening to the periphery of the base layer.

In still another embodiment, a fastening means can be disposed on the upper surface of the base layer along the slit.

In one more embodiment, a fastening means can be disposed on the upper surface of the base layer about the periphery of the base layer.

In an additional embodiment, the fastening means can include a hook or loop configuration.

In one particular embodiment, the upper layer can be coupled to the base layer via a hinge.

In one embodiment, the absorbent stoma pad can have a clamshell shape.

In another embodiment, the absorbent material can be positioned above an upper surface of the external bolster when the absorbent stoma pad encapsulates the external bolster to prevent liquid from contacting the surface of skin.

In an additional embodiment, the base layer can fit between the surface of skin and one or more feet extending from a lower surface of the external bolster.

In one particular embodiment, the base layer can fit between the surface of skin and a lower surface of the external bolster.

In one embodiment, a lower surface of the absorbent material can be in contact with a middle layer, wherein the upper layer and the middle layer encapsulate the absorbent material. The middle layer can include a nonwoven material. For instance, the middle layer can include a spunbond-meltblown-spunbond laminate.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
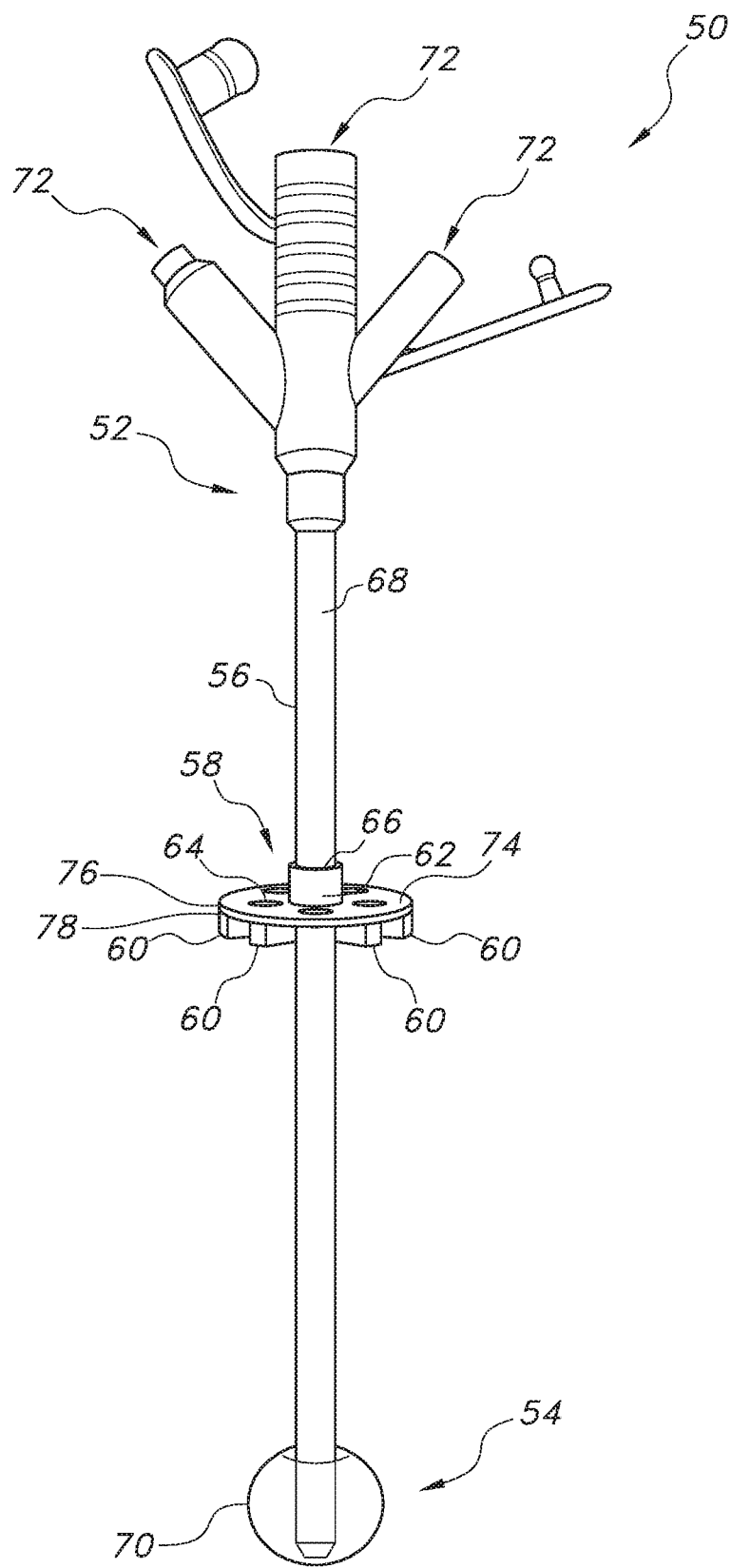
FIG. 1 is a schematic perspective view of a feeding tube with which the absorbent stoma pad of the present invention can be utilized.

Repeat use of reference characters in the present specification and drawings is intended to represent same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention relates to an absorbent stoma pad for encapsulating an external bolster of a feeding tube. The stoma pad includes an upper layer, a base layer, an absorbent material, and a cavity formed between the absorbent material and the base layer. The upper layer contains a centrally located opening with respect to a periphery of the upper layer, wherein the opening is configured to receive a tube portion of the feeding tube. The base layer also contains a centrally located opening with respect to a periphery of the base layer, wherein the opening is also configured to receive the tube portion of the feeding tube. Meanwhile, the absorbent material is disposed adjacent the upper layer's lower surface. Further, the cavity permits airflow between the absorbent layer and the base layer when the external bolster is encapsulated by the stoma pad and positioned within the cavity. An absorbent stoma pad having such a configuration can absorb drainage or leakage from a stoma site, which can, in turn, reduce skin irritation and the occurrence of skin infections at the stoma site. Due to the use of the absorbent stoma pad of the present invention, the skin near the stoma site can be kept dry and ventilated due to the arrangement of the absorbent material and base layer, where the absorbent material is prevented from contacting the base layer and/or skin during use to prevent moisture from being trapped against the skin. The various components of the absorbent stoma pad are discussed in more detail below.

Upper Layer

The upper layer (e.g., the layer located the greatest distance away from the surface of skin) of the absorbent stoma pad can be formed from a non-woven material, where the term nonwoven material refers to a web having a structure of individual fibers or threads which are interlaid, but not in an identifiable manner as in a knitted fabric. Nonwoven fabrics or webs have been formed from many processes such as for example, meltblowing processes, spunbonding processes, through-air bonded carded web (also known as BCW and TABCW) processes, etc. The basis weight of nonwoven materials may generally vary, such as from about 5 grams per square meter ("gsm") to 150 gsm, in some embodiments from about 10 gsm to about 125 gsm, and in some embodiments, from about 20 gsm to about 120 gsm. In one particular embodiment, the nonwoven material can be in the form of a spunbond-meltblown-spunbond (SMS) laminate formed from spunbond and meltblown webs.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, educative drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

The two spunbond layers of the SMS laminate of the upper layer absorbent stoma pad of the present invention can be formed from any suitable polymer that provides softness, stretch, and pliability to the upper layer. For instance, the spunbond layers can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen, et al.; U.S. Pat. No. 5,218,071 to Tsutsui, et al.; U.S. Pat. No. 5,272,236 to Lai et al.; and U.S. Pat. No. 5,278,272 to Lai, et al., which are incorporated herein in their entirety by reference thereto for all purposes.

Of course, the spunbond layers in the upper layer of the absorbent stoma pad are by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the spunbond layers can each include a copolymer of polypropylene and polyethylene.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin, et at; U.S. Pat. No. 5,322,728 to Davis, et al.; U.S. Pat. No. 5,472,775 to Obiieski, et al.; U.S. Pat. No. 5,272,236 to Lai, et al.; and U.S. Pat. No. 6,090,325 to Wheat, et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

The meltblown layer of the spunbond-meltblown-spunbond laminate used to form the upper layer of the absorbent stoma pad can also be formed from any of the semicrystalline polyolefins discussed above with respect to the first and second spunbond layers. In one particular embodiment, the meltblown layer of the SMS laminate can be formed from 100% polypropylene.

Although the upper layer of the absorbent stoma pad is described as being formed from a spunbond-meltblown-spunbond (SMS) laminate, it is to be understood that the upper layer can be formed from any other suitable material, such as any other type of nonwoven material (e.g., a through-air bonded carded web), a woven material, or a film sheet material.

Base Layer

Next, the base layer (e.g., the layer located between the surface of skin and the external bolster of the feeding tube) of the absorbent stoma pad can be a wicking layer that transmits fluid to the absorbent material, which is discussed in more detail below. In other words, the base layer does not retain moisture and instead transfers moisture away from the stoma site and skin surface. For example, the base layer can receive or intake fluid from the stoma site, and capillary action or another fluid transfer mechanism can ensure that the fluid is moved quickly from the base layer to the upper layer where the base layer and upper layer meet or overlap. Then, the fluid can be absorbed by the superabsorbent material as discussed in more detail below, where the fluid does not contact the base layer, surface of skin, or stoma site. The base layer can be formed from any suitable material that can act as a wicking layer so that moisture is quickly moved away from the stoma site toward the absorbent material and so that moisture is not retained against the patient's skin at the stoma site, which can degrade skin health at the stoma site. For example, the base layer can be constructed of any woven, nonwoven or sheet material which is easily penetrated by bodily fluids that may contact the absorbent stoma pad. Examples of suitable topsheet materials include natural fiber webs (such as cotton), rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated films and net materials can also be used, as can laminates of/or combinations of these materials. A specific example of a suitable central topsheet layer material is a bonded carded web (BCW) made of polypropylene and polyethylene such as that obtainable from Sandler Corporation, Germany. U.S. Pat. No. 4,801,494 to Datta, et al. and U.S. Pat. No. 4,908,026 to Sukiennik, et al., and WO 2009/062998 to Texol teach various other topsheet materials that may be used in the present invention, each of which is hereby incorporated by reference in its entirety. The base layer may contain a plurality of apertures formed therethrough to permit body fluid to pass more readily into the absorbent material. The apertures may be randomly or uniformly arranged throughout the base layer. Further, the base layer can have a basis weight ranging from about 10 gsm to about 120 gsm. For instance, in one embodiment, the base layer can be constructed from a through air bonded carded web (TABCW) having a basis weight ranging from about 15 gsm to about 100 gsm. In another embodiment, the base layer can be constructed from a TABCW having a basis weight ranging from about 20 gsm to about 50 gsm.

Absorbent Material

Further, the absorbent material, which can be positioned adjacent a lower surface of the upper layer such that the absorbent material is positioned above the external bolster of the feeding tube and separated from the base layer, can be formed from a superabsorbent material. For instance, an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof can be used in the absorbent stoma pad of the present invention. In a particular embodiment, the absorbent web material can include a matrix of cellulosic fluff and a superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. Examples of suitable superabsorbent materials include poly(acrylic acid) and poly(methacrylic acid), poly(acrylamides), poly(vinyl ethers), maleic anhydride copolymers with vinyl ethers and α-olefins, poly(vinyl pyrrolidone), poly(vinylmorpholinone), poly(vinyl alcohol), and salts and copolymers thereof. Other superabsorbent materials include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum, and so forth. Mixtures of natural and wholly or partially synthetic superabsorbent polymers may also be useful in the present invention.

Regardless of the combination of absorbent materials used in the absorbent stoma pad of the present invention, the absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

It is also to be understood that a middle layer formed from the same materials as the upper layer can be used to sandwich the absorbent material in place above the external bolster. For instance, in some embodiments, the absorbent material can be contacted on its lower surface with an additional material such as middle layer, which can be an SMS layer having the same structure as the upper layer described above. The use of the middle layer can ensure that the absorbent material is encapsulated and does not come into contact with the surface of skin.

Skin Health Additives

It is also to be understood that the base layer, the absorbent material, or both can further include skin health additives. The skin health additives can be incorporated into the base layer or the absorbent material or can be coated onto a skin-facing surface or lower surface of the absorbent material or base layer by any suitable method known in the art. In some embodiments, the base layer, the absorbent material, or both can include an antimicrobial agent, an antifungal agent, or a combination thereof to neutralize any fluid secreted from the stoma site. For instance, antimicrobial agents that can be added to the base layer, the absorbent material, or both can include copper, silver, mild acids and/or bases such as acetic acid, hydrogen peroxide, iodine, triclosan, aluminum chlorohydrate, hexachlorophene, entrained oxygen, or a combination thereof, while antifungal agents that can be added to the base layer, the absorbent material, or both can include sulphur, rosemary oil, tea tree oil, or a combination thereof.

The specific arrangement of the upper layer, base layer, and absorbent material to form the absorbent stoma pad of the present invention is now discussed in reference to the figures.

Referring now to FIG. 1 of the drawings, a schematic perspective view of a feeding tube 50 with which the absorbent stoma pad of the present invention can be utilized is shown for reference. The feeding tube 50 includes an external end 52 and an internal end 54 between which a tube 56 extends, where the tube 56 has a lumen 68 for delivering food, medication, or both to a patient via one or more ports 72. The external end 52 includes an external bolster 58 that can be positioned adjacent a surface of a patient's skin 84 (see FIG. 2), while the internal end 54 includes a retention balloon 70 that can be positioned adjacent the patient's stomach wall 82 (see FIG. 2). The external bolster 58 and retention balloon 70 hold the feeding tube 50 in place in a tract formed at stoma site 86 (see FIG. 2). The external bolster 58 can include a base 74 having an upper surface 76 and a lower surface 78. A sleeve 62 can be positioned against the upper surface 76 to receive the tube 56, and the base 74 can include a bore or opening 66 through which the tube 56 can pass, where the tube 56 enters the patient's stomach by passing through the abdominal wall 80 and the stomach wall 82. The base 74 can also include air holes 64 that extend from the upper surface 76 to the lower surface 78 of the base 74, where the air holes 64 facilitate air flow around a stoma site 86 (see FIG. 2). Although not required, multiple feet 60 can extend from the lower surface 78 of the base 74 of the external bolster 58, where the feet 60 can prevent the base 74 from contacting the stoma site 86 (see FIG. 2) and minimize the amount of contact between the surface of the patient's skin 84 and the external bolster 58, which can improve aeration of the stoma site 86 (see FIG. 2). As discussed above, fluid can leak from the stoma site 86, which can lead to skin infections and poor stoma health in general. As such, the absorbent stoma pad of the present invention can be used in conjunction with the feeding tube 50 of FIG. 1 to absorb any leakage from the stoma site 86.

Figure 2:
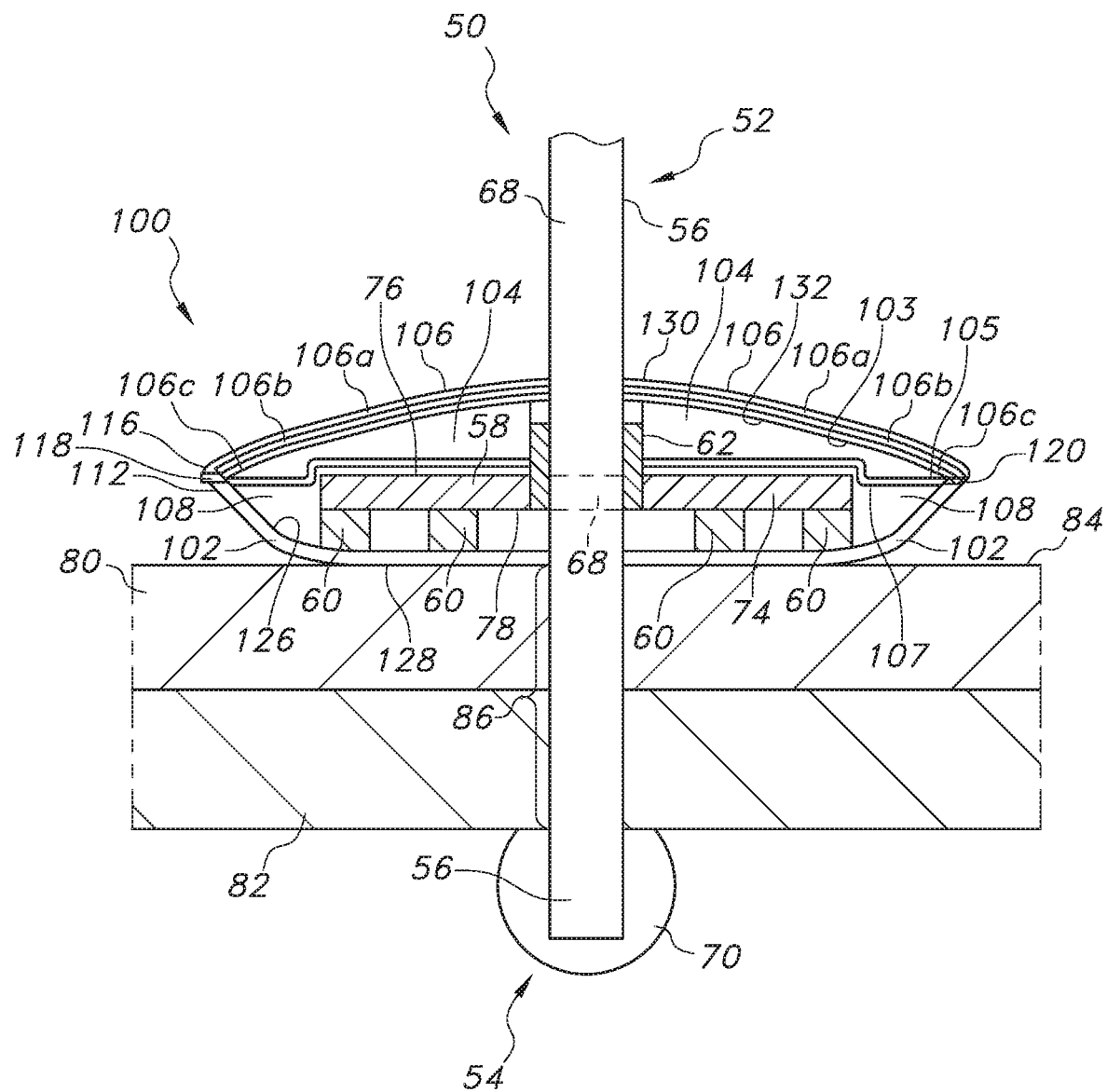
FIG. 2 is a schematic cross-sectional view of a portion of the feeding tube of FIG. 1 and the absorbent stoma pad of the present invention in use.

Turning now to FIG. 2, a schematic cross-sectional view of a portion of the feeding tube 50 of FIG. 1 and the absorbent stoma pad 100 of the present invention in use is shown. The absorbent stoma pad 100 includes a base layer 102, an upper layer 106, and an absorbent material 104 positioned adjacent the upper layer 106 such that the absorbent material 104 is separated from the base layer 102 and can surround the sleeve 62 of the external bolster 58 and can be positioned above the base 74 of the external bolster 58 when in use. The base layer 102 includes a lower surface 128 that faces the surface of the patient's skin 84 and an upper surface 126 that faces away from the surface of the patient's skin 84 when the absorbent stoma pad is used to encapsulate the feeding tube 50. In one particular embodiment, the upper layer 106 can be in the form of an SMS laminate having a spunbond layer 106a, a meltblown layer 106b, and a spunbond layer 106c. An upper surface 103 of the absorbent material 104 can be disposed on a lower surface 132 of the upper layer 106, while the upper surface 130 of the upper layer 106 faces the outside environment. As shown in FIG. 2, the absorbent stoma pad 100 has a clamshell shape such that a cavity 108 is formed between an upper surface 126 of the base layer 102 and the absorbent material 104 to permit airflow around the external bolster 58. Further, the upper surface 103 of the absorbent material 104 is positioned on the lower surface 132 of the upper layer 106 such that the absorbent material 104 is disposed above the upper surface 76 of the base 74 of the external bolster 58 during use to prevent liquid from contacting the surface of skin 84, as any liquid absorbed by the stoma pad 100 will be retained within the absorbent material 104. In other words, there is no contact between the absorbent material 104 and the base layer 106 to prevent the liquid absorbed from the stoma site 86 from contacting the surface of skin 84 through the base layer 102. Further, in some embodiments, the absorbent material 104 can be contacted on its lower surface 105 with an additional material such as middle layer 107, which can be an SMS layer having the same structure as upper layer 106. The use of the middle layer 107 can ensure that the absorbent material 104 is encapsulated and does not come into contact with the surface of skin 84. Meanwhile, as shown in FIG. 2, the lower surface 128 of the base layer 102 contacts the surface of skin 84, while the upper surface 126 of the base layer 102 can contact the feet 60 (if present) of the external bolster 58 such that the base layer 102 fits between the surface of skin 84 and the feet 60 of the external bolster 58 when the stoma pad 100 is in use to encapsulate the external bolster 58. In another embodiment, such as when stoma pad 100 is used in conjunction with a bolster 58 that does not contain feet 60, the lower surface 128 of the base layer 102 contacts the surface of skin 84, while the upper surface 126 of the base layer 102 can contact the lower surface 78 of the bolster 58 such that the base layer 102 fits between the surface of skin 84 and the lower surface 78 of the base layer 102 when the stoma pad 100 is in use to encapsulate the external bolster 58.

Figure 3:
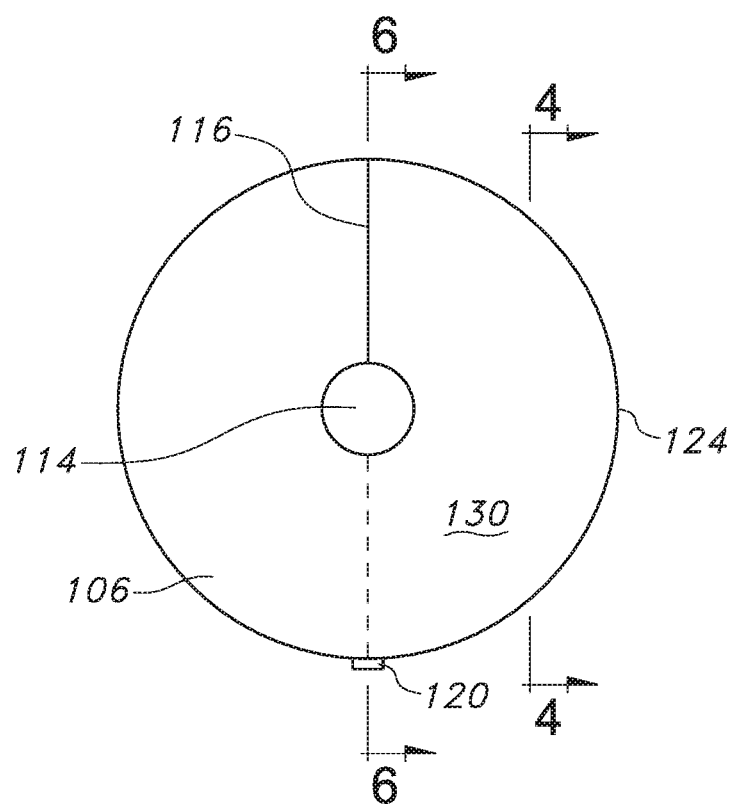
FIG. 3 is a top view of the upper (SMS) layer of the absorbent stoma pad of the present invention.
Figure 4:
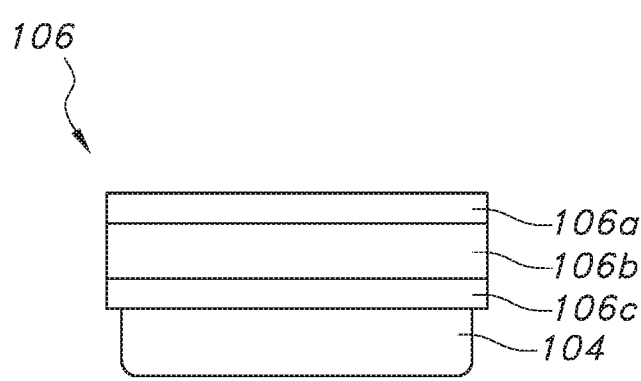
FIG. 4 is a cross-sectional view of the upper (SMS) layer of the absorbent stoma pad of the present invention as shown in FIG. 3 as taken from cut line 4-4.

The specific features of the upper layer 106 will now be discussed with reference to FIGS. 3, 4, and 7. For instance, FIG. 3 is a top view of upper surface 130 of the upper (SMS) layer 106 of the absorbent stoma pad 100 of the present invention, FIG. 4 is a cross-sectional view of the upper (SMS) layer 106 of the absorbent stoma pad 100 of the present invention as shown in FIG. 3 and taken from cut line 4-4 to shown a spunbond layer 106a and a spunbond layer 106c with a meltblown layer 106b disposed therebetween, where the absorbent material 104 is disposed on the spunbond layer 106c. Meanwhile, FIG. 7 is a bottom view of the lower surface 132 of the upper (SMS) layer 106 of the absorbent stoma pad 100 of the present invention, without the absorbent material 104 shown attached thereto.

As shown in FIG. 3, the upper layer 106 can include a centrally located opening 114 for receiving the tube 56 of the feeding tube 50 of FIG. 1. Further, a slit 116 can extend from the opening 114 to the periphery 124 of the upper layer 106, and a portion of a hinge 120 can be located at the periphery 124, where the hinge 120 connects the upper layer 106 of the absorbent stoma pad 100 to the base layer 102 of the absorbent stoma pad 100. Although not required, the slit 116 can be positioned about 180° from the portion of the hinge 120 that connects the upper layer 106 to the base layer 102. The slit 116 can allow the upper layer 106 of the absorbent stoma pad 100 to pass around the tube 56 of the feeding tube 50 above the upper surface 76 of the external bolster 58 (see FIG. 2), while the hinge 120 facilitates the encapsulation of the external bolster 58 by the upper layer 106 and the base layer 102 in that it allows the absorbent stoma pad 100 to open and close in a manner similar to a clamshell in order to slide the base layer 102 underneath the feet 60 of the external bolster 58 and position the upper layer 106 around the upper surface 76 of the external bolster 58.

Figure 7:
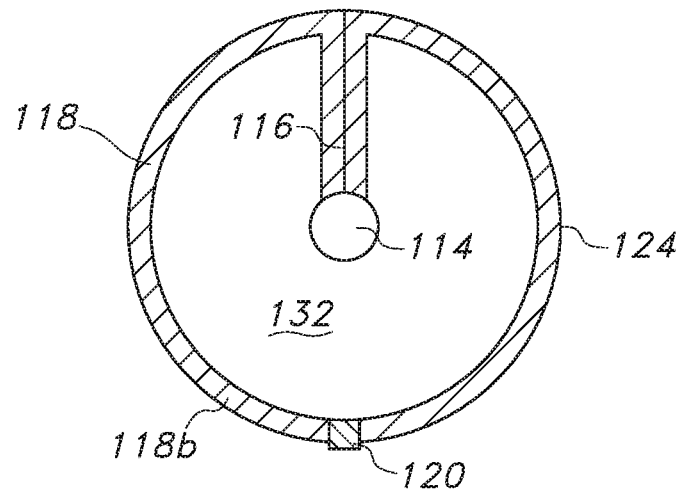
FIG. 7 is a bottom view of the upper (SMS) layer of the absorbent stoma pad of the present invention.

Turning now to FIG. 7, the lower surface 132 of the upper layer 106 is shown. As illustrated in FIG. 7, a fastening means 118 can be disposed about the periphery 124 of the lower surface 132 of the upper layer 106. Although shown in the form of loops 118b, it is to be understood that any other suitable fastening means 118 can be used, such as hooks, adhesive, tape, etc. The fastening means 118 can also be disposed on the lower surface 132 of the upper layer 106 on one or both sides of the slit 116, where the fastening means 118 extends from the opening 114 to the periphery 124 along the slit 116. The fastening means 118 facilitate the secure attachment of the periphery 124 of the upper layer 106 of the absorbent stoma pad 100 to the periphery 122 of the base layer 102 of the absorbent stoma pad 100 in order to encapsulate the external bolster 58 of the feeding tube 50.

The specific features of the base layer 102 will now be discussed with reference to FIGS. 5 and 8. For instance, FIG. 5 is a bottom view of the base layer 102 of the absorbent stoma pad 100 of the present invention while FIG. 8 is a top view of the base layer 102 of the absorbent stoma pad 100 of the present invention.

Figure 5:
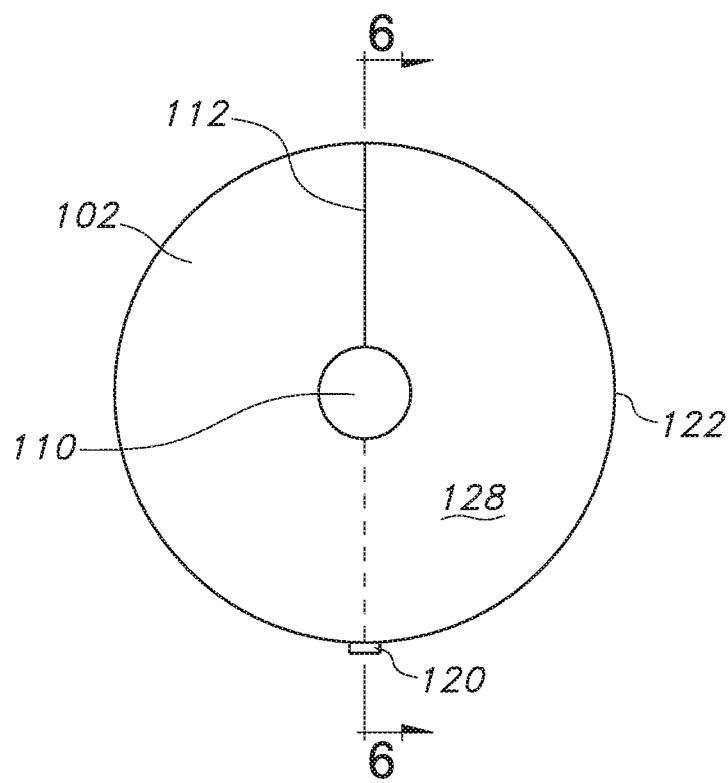
FIG. 5 is a bottom view of the base layer of the absorbent stoma pad of the present invention.

As shown in FIG. 5, the base layer 102 can include a centrally located opening 110 for receiving the tube 56 of the feeding tube 50 of FIG. 1. Further, a slit 112 can extend from the opening 110 to the periphery 122 of the base layer 102, and a portion of a hinge 120 can be located at the periphery 122, where the hinge 120 connects the base layer 102 of the absorbent stoma pad 100 to the upper layer 106 of the absorbent stoma pad 100. Although not required, the slit 112 can be positioned about 180° from the portion of the hinge 120 that connects the base layer 102 to the upper layer 106. The slit 112 can allow the base layer 102 of the absorbent stoma pad 100 to pass around the tube 56 of the feeding tube 50 below the lower surface 78 of the external bolster 58 (see FIG. 2), while the hinge 120 facilitates the encapsulation of the external bolster 58 by the base layer 102 and the upper layer 106 in that it allows the absorbent stoma pad 100 to open and close in a manner similar to a clamshell in order to slide the base layer 102 underneath the feet 60 of the external bolster 58 and position the upper layer 106 around the upper surface 76 of the external bolster 58.

Figure 8:
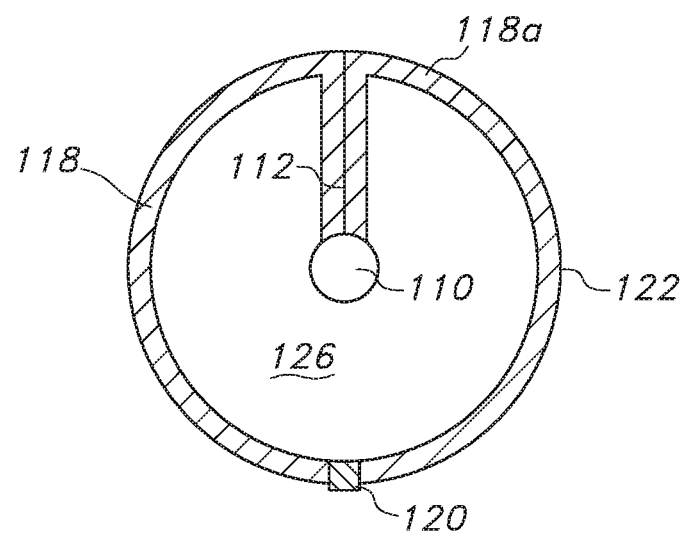
FIG. 8 is a top view of the base layer of the absorbent stoma pad of the present invention.

Turning now to FIG. 8, the upper surface 126 of the base layer 102 is shown. As illustrated in FIG. 8, a fastening means 118 can be disposed about the periphery 122 of the upper surface 126 of the base layer 102. Although shown in the form of hooks 118a, it is to be understood that any other suitable fastening means 118 can be used, such as loops, adhesive, tape, etc. The fastening means 118 can also be disposed on the upper surface 126 of the base layer 102 on one or both sides of the slit 112, where the fastening means 118 extends from the opening 110 to the periphery 122 along the slit 112. The fastening means 118 facilitate the secure attachment of the periphery 122 of the base layer 102 of the absorbent stoma pad 100 to the periphery 124 of the upper layer 106 of the absorbent stoma pad 100 in order to encapsulate the external bolster 58 of the feeding tube 50.

Figure 6:
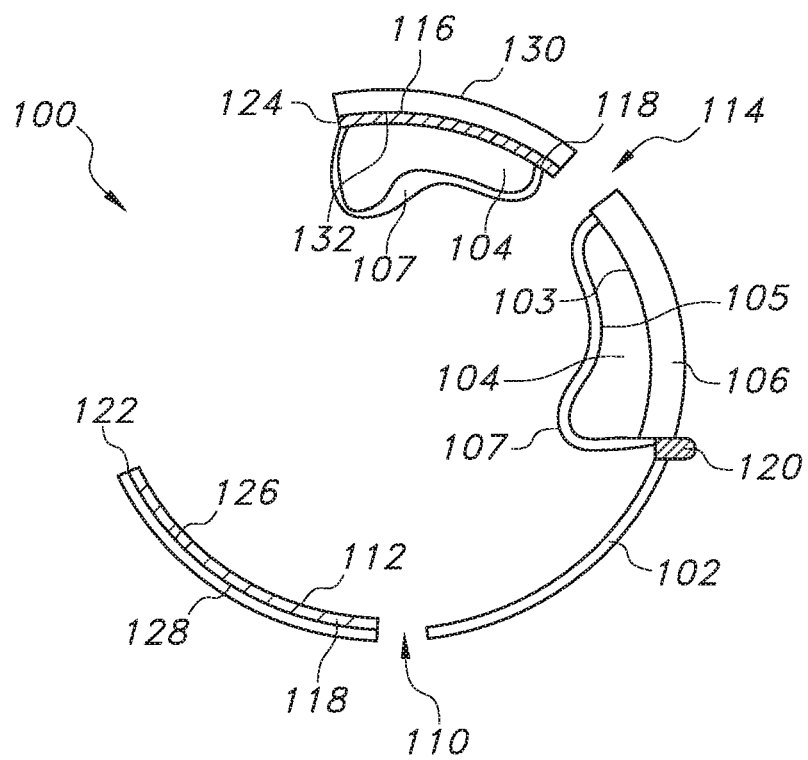
FIG. 6 is a cross-sectional view of the absorbent stoma pad of the present invention before it has been used in conjunction with a feeding tube, such as the feeding tube of FIG. 1.

Referring now to FIG. 6, a cross-sectional view of the absorbent stoma pad 100 of the present invention taken at cut line 6-6 intersecting the slits 112 and 116 in FIGS. 3 and 5 before the absorbent stoma pad 100 has been used in conjunction with a feeding tube, such as the feeding tube 50 of FIG. 1, is illustrated. Specifically, FIG. 6 shows the clamshell shape of the absorbent stoma pad 100, where the upper layer 106 and base layer 102 are joined at hinge 120, where the hinge 120 facilitates the encapsulation of an external bolster 58 of a feeding tube 50 by the absorbent stoma pad 100. FIG. 6 also shows the presence of fastening means 118 extending along the slit 112 in the base layer 102 to the periphery 122 and the presence of fastening means 118 extending along the slit 116 in the upper layer 106 to the periphery 124, where it is to be understood that the fastening means 118 can also be used to secure the periphery 122 of the base layer 102 to the periphery 124 of the upper layer 106 once the external bolster 58 has been encapsulated by the absorbent stoma pad 100. The positioning of the absorbent material 104 such that its upper surface 103 is in contact with the lower surface 132 of the upper layer 106 and so that its lower surface 104 is in contact with middle layer 107 is also shown in FIG. 6.

Figure 9:
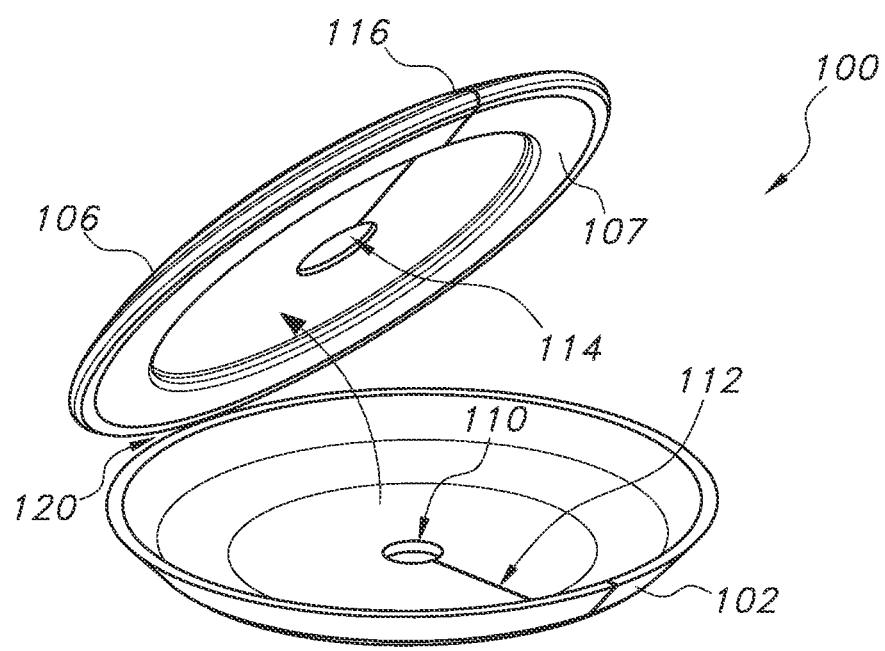
FIG. 9 is a perspective view of the absorbent stoma pad of the present invention when in an open position (e.g., before encapsulating an external bolster of a feeding tube with the absorbent stoma pad).
Figure 10:
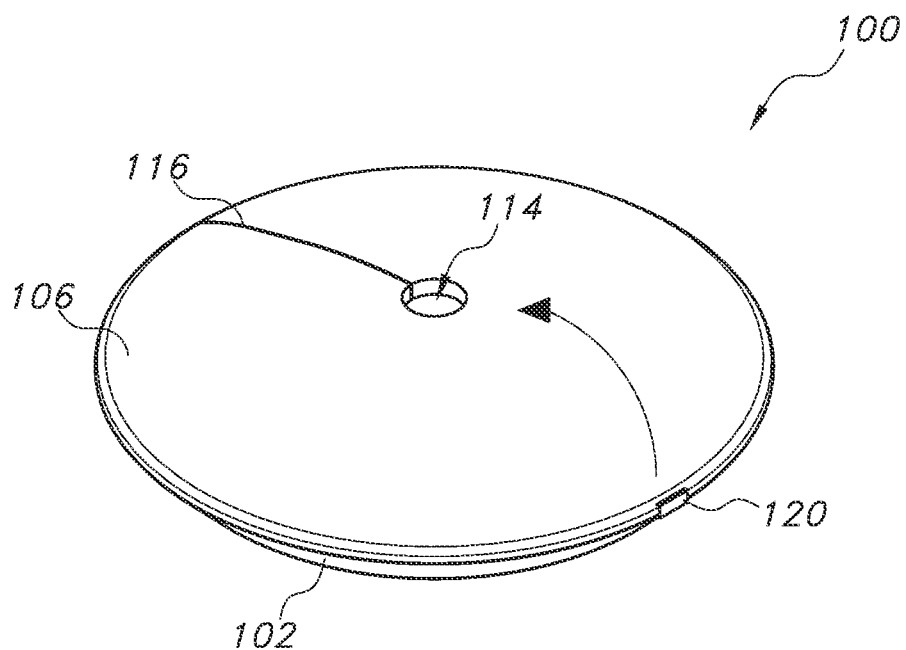
FIG. 10 is a perspective view of the absorbent stoma pad of the present invention when in a closed position (e.g., after encapsulating an external bolster of a feeding tube with the absorbent stoma pad).

FIG. 9 is a perspective view of the absorbent stoma pad 100 of the present invention when in an open position (e.g., before encapsulating an external bolster 58 of a feeding tube 50 with the absorbent stoma pad 100), while FIG. 10 is a perspective view of the absorbent stoma pad 100 of the present invention when in a closed position (e.g., after encapsulating an external bolster 58 of a feeding tube 50 with the absorbent stoma pad 100). FIGS. 9 and 10 show the clamshell shape of the absorbent stoma pad 100, which enables the absorbent stoma pad 100 to encapsulate the external bolster 58 of the feeding tube 50 shown in FIGS. 1-2.

Further, although shown in use with a feeding tube with an external bolster having feet that are positioned adjacent a surface of skin, where the feeding tube has an external end and an internal end, it is also to be understood that the stoma pad can be used in conjunction with any type of feeding tube. For instance, the stoma pad of the present invention can be used with a low profile feeding tube with an external bolster that does not have feet and where the tube portion is only located on the external end of the feeding tub and does not extend through the external bolster, the abdominal wall, or the stomach wall.

While various patents have been incorporated herein by reference, to the extent there is any inconsistency between incorporated material and that of the written specification, the written specification shall control. Further, this written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An absorbent stoma pad for encapsulating an external bolster of a feeding tube, wherein the feeding tube further includes a tube portion, wherein the external bolster is positioned above a surface of skin, wherein the absorbent stoma pad comprises:
   an upper layer having an upper surface and a lower surface, wherein the upper layer contains an opening that is centrally located with respect to a periphery of the upper layer, wherein the opening is configured to receive the tube portion of the feeding tube;
   a base layer having an upper surface and a lower surface, wherein the base layer contains an opening that is centrally located with respect to a periphery of the base layer, wherein the opening is configured to receive the tube portion of the feeding tube, wherein the base layer is located adjacent the surface of skin;
   an absorbent material disposed adjacent the lower surface of the upper layer; and
   a cavity separating the absorbent material and the base layer, wherein the cavity permits airflow between the absorbent material and the base layer when the external bolster is encapsulated by the absorbent stoma pad and positioned within the cavity.

2. The absorbent stoma pad of claim 1, wherein the lower surface of the base layer contacts the surface of skin when the external bolster is encapsulated by the upper layer and the base layer of the absorbent stoma pad.

3. The absorbent stoma pad of claim 1, wherein the upper layer comprises a nonwoven material.

4. The absorbent stoma pad of claim 3, wherein the upper layer comprises a spunbond-meltblown-spunbond laminate.

5. The absorbent stoma pad of claim 1, wherein the base layer is a wicking layer, wherein the wicking layer comprises rayon, polyester, a polyolefin, an aliphatic ester, or a combination thereof.

6. The absorbent stoma pad of claim 1, wherein skin health additives are incorporated into the base layer.

7. The absorbent stoma pad of claim 1, wherein the absorbent material is a superabsorbent material.

8. The absorbent stoma pad of claim 7, wherein the superabsorbent material comprises poly(acrylic acid), poly(methacrylic acid), poly(acrylamide), poly(vinyl ether), a maleic anhydride copolymer with a vinyl ether and $\alpha$-olefin, poly(vinyl pyrrolidone), poly(vinylmorpholinone), poly(vinyl alcohol), hydrolyzed acrylonitrile-grafted starch, acrylic acid-grafted starch, methyl cellulose, chitosan, carboxymethyl cellulose, hydroxypropyl cellulose, alginate, xanthan gum, locust bean gum, or a combination thereof.

9. The absorbent stoma pad of claim 1, wherein skin health additives are incorporated into the absorbent material.

10. The absorbent stoma pad of claim 1, wherein the upper layer includes a slit extending from the opening to the periphery of the upper layer, wherein a fastening means is disposed on the lower surface of the upper layer along the slit.

11. The absorbent stoma pad of claim 1, wherein a fastening means is disposed on the lower surface of the upper layer about the periphery of the upper layer.

12. The absorbent stoma pad of claim 1, wherein the base layer includes a slit extending from the opening to the periphery of the base layer, wherein a fastening means is disposed on the upper surface of the base layer along the slit.

13. The absorbent stoma pad of claim 12, wherein the fastening means comprises a hook or loop configuration.

14. The absorbent stoma pad of claim 1, wherein a fastening means is disposed on the upper surface of the base layer about the periphery of the base layer.

15. The absorbent stoma pad of claim 1, wherein the upper layer is coupled to the base layer via a hinge.

16. The absorbent stoma pad of claim 1, wherein the absorbent stoma pad has a clamshell shape.

17. The absorbent stoma pad of claim 1, wherein the absorbent material is positioned above an upper surface of the external bolster when the absorbent stoma pad encapsulates the external bolster to prevent liquid from contacting the surface of skin.

18. The absorbent stoma pad of claim 1, wherein the base layer fits between the surface of skin and one or more feet extending from a lower surface of the external bolster.

19. The absorbent stoma pad of claim 1, wherein the base layer fits between the surface of skin and a lower surface of the external bolster.

20. The absorbent stoma pad of claim 1, wherein a lower surface of the absorbent material is in contact with a middle layer, wherein the upper layer and the middle layer encapsulate the absorbent material, wherein the middle layer comprises a nonwoven material.

* * * * *